(12) United States Patent
Stokes et al.

(10) Patent No.: US 6,672,344 B1
(45) Date of Patent: Jan. 6, 2004

(54) ROBOTIC SYSTEM HAVING POSITIONALLY ADJUSTABLE MULTIPLE PROBES

(75) Inventors: Jeffrey H. Stokes, Franklin, MA (US); Thomas R. Londo, Ashland, MA (US)

(73) Assignee: PerSeptive Biosystems, Inc., Framingham, MA (US)

( * ) Notice: Subject to any disclaimer, the term of this patent is extended or adjusted under 35 U.S.C. 154(b) by 103 days.

(21) Appl. No.: 10/045,518

(22) Filed: Oct. 26, 2001

(51) Int. Cl.[7] .................................................. B65B 3/04
(52) U.S. Cl. .............................. 141/234; 141/9; 141/94; 141/279; 73/863.01; 422/100; 436/180
(58) Field of Search ....................... 141/1, 9, 94, 100, 141/192, 193, 234, 235, 237, 238, 242, 250, 266, 279, 284; 73/863.01, 863.31; 422/100; 436/180

(56) References Cited

U.S. PATENT DOCUMENTS

| | | | | |
|---|---|---|---|---|
| 4,586,546 A | * | 5/1986 | Mezei et al. ................... | 141/2 |
| 4,621,665 A | * | 11/1986 | Webb ............................. | 141/1 |
| 5,957,167 A | * | 9/1999 | Feygin ........................ | 141/31 |
| 6,143,252 A | * | 11/2000 | Haxo et al. ................. | 422/131 |

* cited by examiner

Primary Examiner—Gregory L. Huson
Assistant Examiner—Peter deVore
(74) Attorney, Agent, or Firm—Andrew T. Karnakis

(57) ABSTRACT

An array of probes is provided wherein the probes are maintained in place in bores extending through a housing by a friction force applied to the probes. The friction force can be overcome by another force applied to the probes, thereby allowing the probes to move to a new position within the bore. In one embodiment, the probes contain an internal conduit through which liquid samples are introduced into the probes. Thereafter, the probes are moved to contact a substrate surface to move the probes to a new position, the configuration of which replicates the substrate surface configuration. The housing is then raised a predetermined distance to allow sample to be accurately deposited on the substrate surface from a desired height above the substrate surface. The probes are then returned to their original position.

20 Claims, 4 Drawing Sheets

ROBOTIC SYSTEM HAVING POSITIONALLY ADJUSTABLE MULTIPLE PROBES

BACKGROUND OF THE INVENTION

This invention relates to a positionally adjustable set of multiple probes particularly suitable for delivering multiple liquid samples, a system incorporating the probes and a process for utilizing the probes.

Prior to the present invention, robots have been used in numerous applications to reduce the labor required for repetitive sample processing. One such application involves processing and spotting samples for analysis by mass spectrometry (MS) from micro titer plates (MTP) on to Matrix-Assisted Laser/Desorption Ionization (MALDI) sample plates. Historically to assure proper sample spotting a robot end-user doing MALDI MS would need to conduct a height calibration for specific sample plates in specific racks on the robot deck to "teach" the robot where the surface of the sample plate was located in relation to the outlet end of a hollow robotic probe. Having determined the height calibration, the robot would attempt to dispense a small volume of liquid onto the surface of the plate by positioning the hollow probe containing a liquid sample just above the surface and then allowing a hanging drop of the sample to touch the surface, thus causing it to stick and be deposited on the surface. Robotic workstations can hold many racks, which typically hold many sample plates and can be moved to different locations on the robot deck. Even if the software controlling the robot could make the multiple height calibrations required, the operator would be required to conduct the calibration every time the plate or probe is relocated or replaced.

Sample delivering robotic systems become more complicated when multiple probes (e.g., a one by four row) which move in the Z direction (i.e., up or down) with respect to the robot deck are used in the system, particularly when such probes are rigidly attached to a robotic arm. Even if the multiple probes could be perfectly aligned to each other, only one probe would theoretically be positioned in a plane parallel with the receiving sample plate. Because the row of probe tips will not be in a parallel plane, the distance from tips to plate will vary. If the distance is too great, the droplet of sample will not touch the plate and hence the liquid sample will not spot. Conversely, if there is no distance between the probe and plate, or if this distance is too close, then the chemistry previously deposited on the surface could be damaged or the sample may not deposit or deposit off position. Variations that result from manufacturing the robotic system, the racks and the sample plates have proven to be too great to attain the perfect relative positioning between a sample plate and an array of multiple probes. Matters are even more complicated when probes that are assembled as a three-dimensional array, for example in a four by four arrangement, are moved in the Z direction.

It would be desirable to provide a robotic apparatus, system and process which includes an array of multiple probes for delivering liquid samples which can be positioned at a desired position quickly and automatically. In addition, it would be desirable to provide such an apparatus, system and process wherein the multiple probes can be accurately positioned simultaneously rather than individually.

BRIEF DESCRIPTION OF THE INVENTION

This invention provides an array of probes capable of simultaneously delivering a plurality of samples to a substrate surface wherein the distance between the outlet end of each probe and the substrate surface is essentially the same for each probe. This distance can be accurately controlled each time the substrate surface is replaced with a new substrate surface. The probes are slidably mounted within a probe housing such that the outlet end of each probe is exposed to allow interaction with the substrate surface, and a wall of the probe is contacted with a friction element which exerts a friction force on the probe to retain the probe in place within the housing. In one embodiment, the probes are hollow tubes and an inlet end of the probe is secured to a flexible conduit which permits movement of the probe and which delivers fluid to the probe or removes fluid from the probe. Movement of the probes from an initial position is effected by the application of a second force that is sufficient to overcome the friction force exerted on the probe wall. When the second force is no longer applied to the probes, the friction force retains the probes at a new position.

For the fluid dispense embodiment discussed above, a cycle for using the probe comprises drawing a vacuum within the probe through the flexible conduits in order to aspirate air into the probes. The air functions as a barrier between a wash liquid and a liquid sample within the probe. The robotic system positions the probe housing over the MTP to allow the probes to aspirate liquid sample from the MTP. Thereafter the probe housing is positioned over a MALDI sample plate and the probe housing is lowered such that the probes are then allowed to contact the surface of the sample plate. The force applied to lower the probes is sufficiently large to overcome the friction force exerted by the friction element so that the probes are moved to come in contact with the substrate surface. Since the position of the substrate surface within the robotic system is almost always nonparallel with the ends of the probes, the outlet ends of the probes will be in different positions and thus the robotic system overdrives the lowering probes to make sure that each probe in the array comes in contact with the substrate surface. The probes are then raised to position the outlet ends of each of the probes at a desired distance from the substrate surface, such as about 0.01 inch from the surface. A positive pressure is then applied to the probe so that the liquid samples are deposited on the substrate surface, such as on a plurality of shallow wells on the MALDI sample plate surface. The probe housing is then raised and a plate integral with the probe housing contacts a fixed surface which moves and resets the probes to their initial position. The probes are then directed to a waste container whereupon the pressure within the probe is increased in order to deliver wash liquid from the flexible conduits through the probes to render them sufficiently clean to process additional samples without contamination. The cycle then is repeated with a replacement sample plate being positioned within the robotic system for sample spotting.

The use of the friction element and the fixed surface to reset the probes permits repeated use of the probes wherein the probes are moved simultaneously to adjust to the surface configuration of a given substrate surface without the need to calibrate the position of each probe individually.

DESCRIPTION OF SPECIFIC EMBODIMENTS

Figure 1:
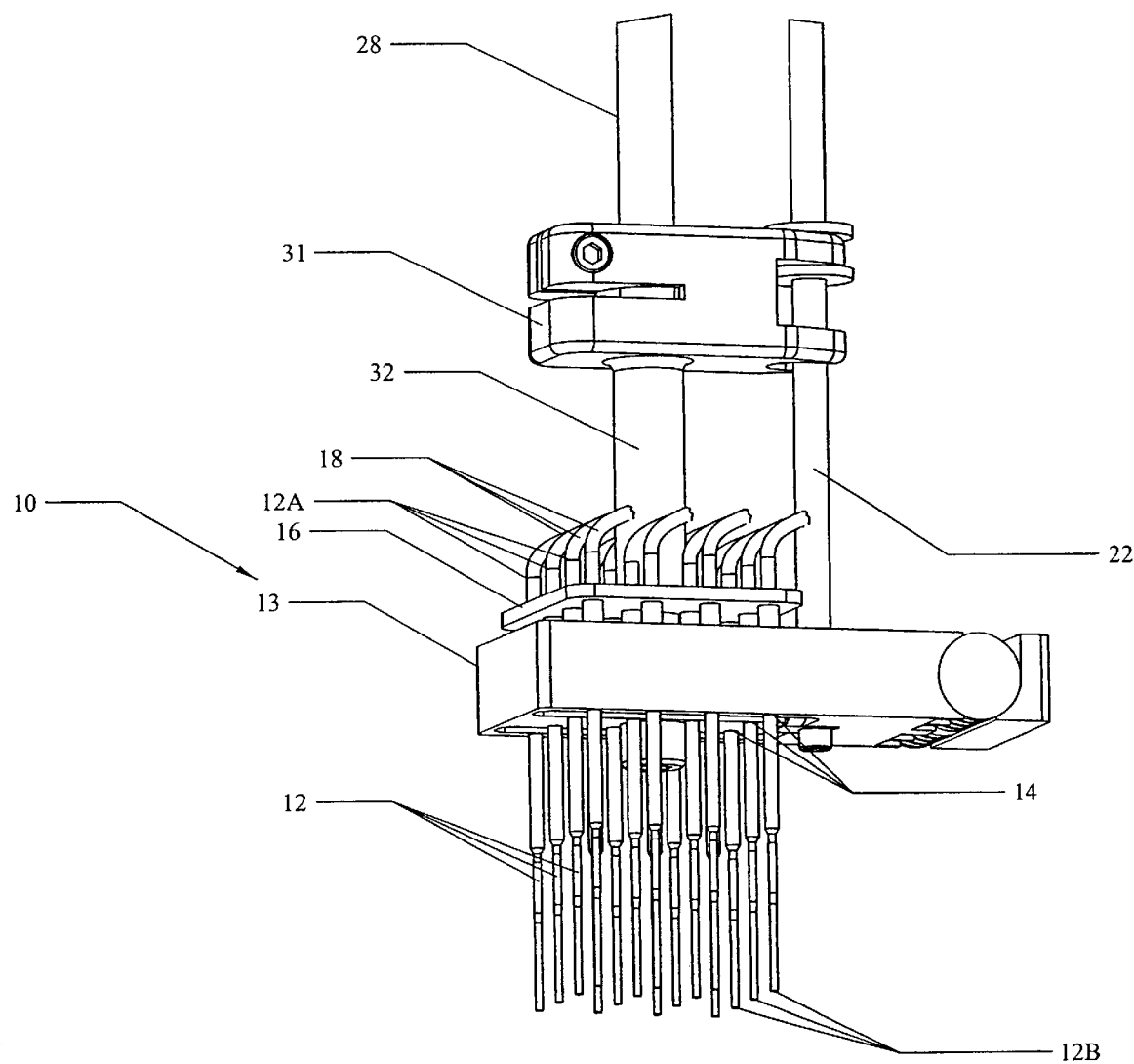
FIG. 1 is a perspective side view of the multiple probe arrangement of a preferred embodiment of the present invention.

The present invention is based on the discovery that a plurality of probes can be accurately and simultaneously positioned by controlling the application of forces acting on the probes along the Z direction of movement of the probes. The probes are initially positioned within a probe housing by an element such as a spring that exerts a frictional force to initially retain the probes in the housing. The frictional force is characterized by force vectors that include a normal component perpendicular to the outer wall of the probe and an axial component along the longitudinal axis of the probes. The frictional force is sufficient to surmount the effects of gravity and to thus hold the probes in position; however, the axial component of the frictional force can be overcome by the application of a second force to allow the probes to be non-destructively moved from their initial position. The probes can thus be moved either up or down in the Z direction by the application of a controlled force from their initial position in a controlled manner, thereby allowing all the probes to be positioned and maintained at a desired height to deposit a liquid sample on a substrate surface such as a MALDI sample plate. This arrangement also permits the probes to return to their initial position for subsequent deposition of a liquid sample on a second substrate surface. The substrate surface includes discrete regions such as wells to isolate samples from each other so that the samples can be individually analyzed.

One important aspect of this invention is that it provides for positioning a plurality of probes simultaneously at a precise position above a substrate surface so that a liquid sample dispensed from the probes can be simultaneously deposited onto a substrate surface in a manner that does not undesirably alter the sample that would thus prevent its accurate analysis. The result is attained by providing an apparatus, system and process which effects accurate deposition of a plurality of samples onto a substrate surface followed by accurate deposition on subsequently presented substrate surfaces in a manner which permits accurate analysis of the samples. The use of multiple probes significantly enhances the analysis throughput. Accurate deposition of the samples depends primarily upon controlling the distance between the outlet end of each of the probes and the surface of the substrate surface receiving the samples for subsequent analysis.

The desired position of the outlet end of each probe relative to the substrate surface is effected by lowering the probe housing to create contact between the outlet ends of the probes and the substrate surface under a sufficient force. The force applied to the outlet ends can be the result of a motor such as a stepper motor driving the probe housing (and hence the probes) downward in the Z direction to create axial forces on the probes upon contact with the substrate. After initial contact with the substrate, the probe housing is overdriven to an even lower position to ensure that all probes in the multi-probe array have contacted the substrate surface. The net effect of this movement is that the probes are moved so that their configuration corresponds to the substrate surface contour and thus enabling the probes to replicate the plane of the sample plate surface. The downward axial force resulting from substrate contact by the probes is sufficient to overcome the sum of the axial component of the frictional force applied to the probes and the gravity effects of the weight of the probes. When the array of probes is moved upwardly in the Z direction a desired distance from the substrate surface, the frictional force overcomes any gravity effects and assures that the height of each probe above the substrate is the same. The liquid samples are then delivered from the probes to the substrate surface in a manner that promotes accurate sample analysis. After the position of the probes is reset to their initial position, the probes are cleaned with a liquid wash. The cycle is then repeated with the position of the probes being altered for a new substrate surface to achieve the correct distance between a the probes and the new substrate surface, and a new set of liquid samples is deposited on the new substrate surface for analysis in the same manner described above.

Figure 2:
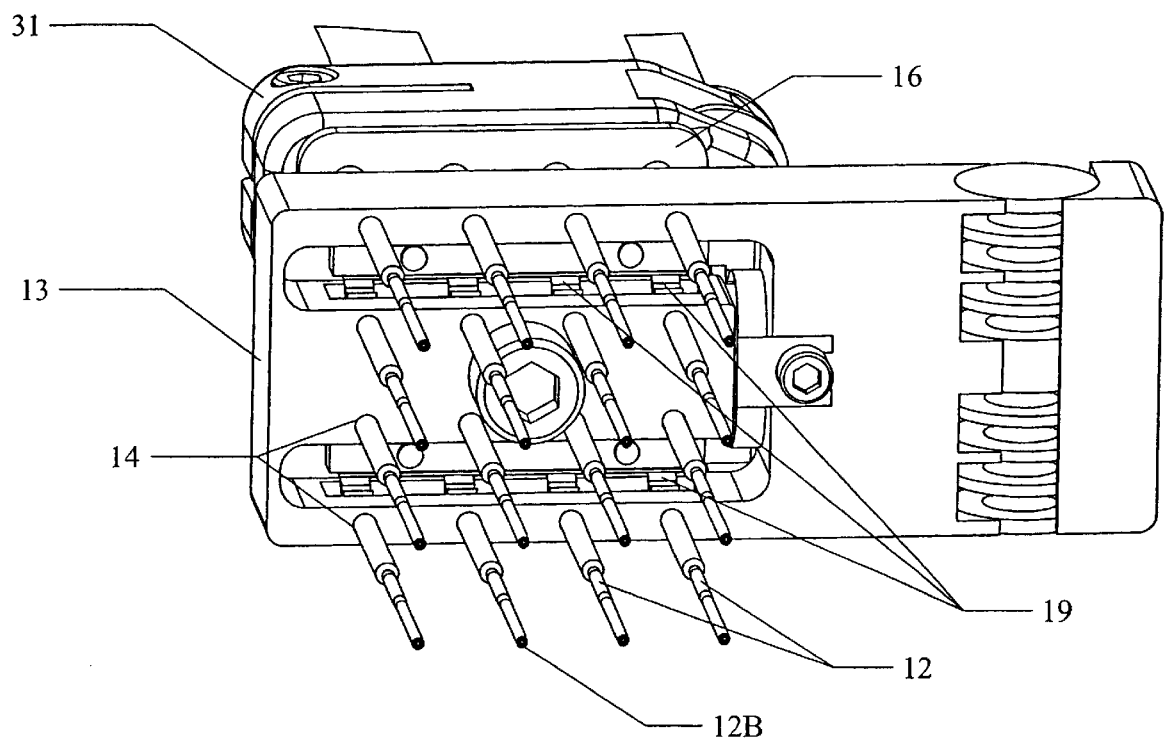
FIG. 2 is a view from below the probes and probe housing of the embodiment shown in FIG. 1.
Figure 4:
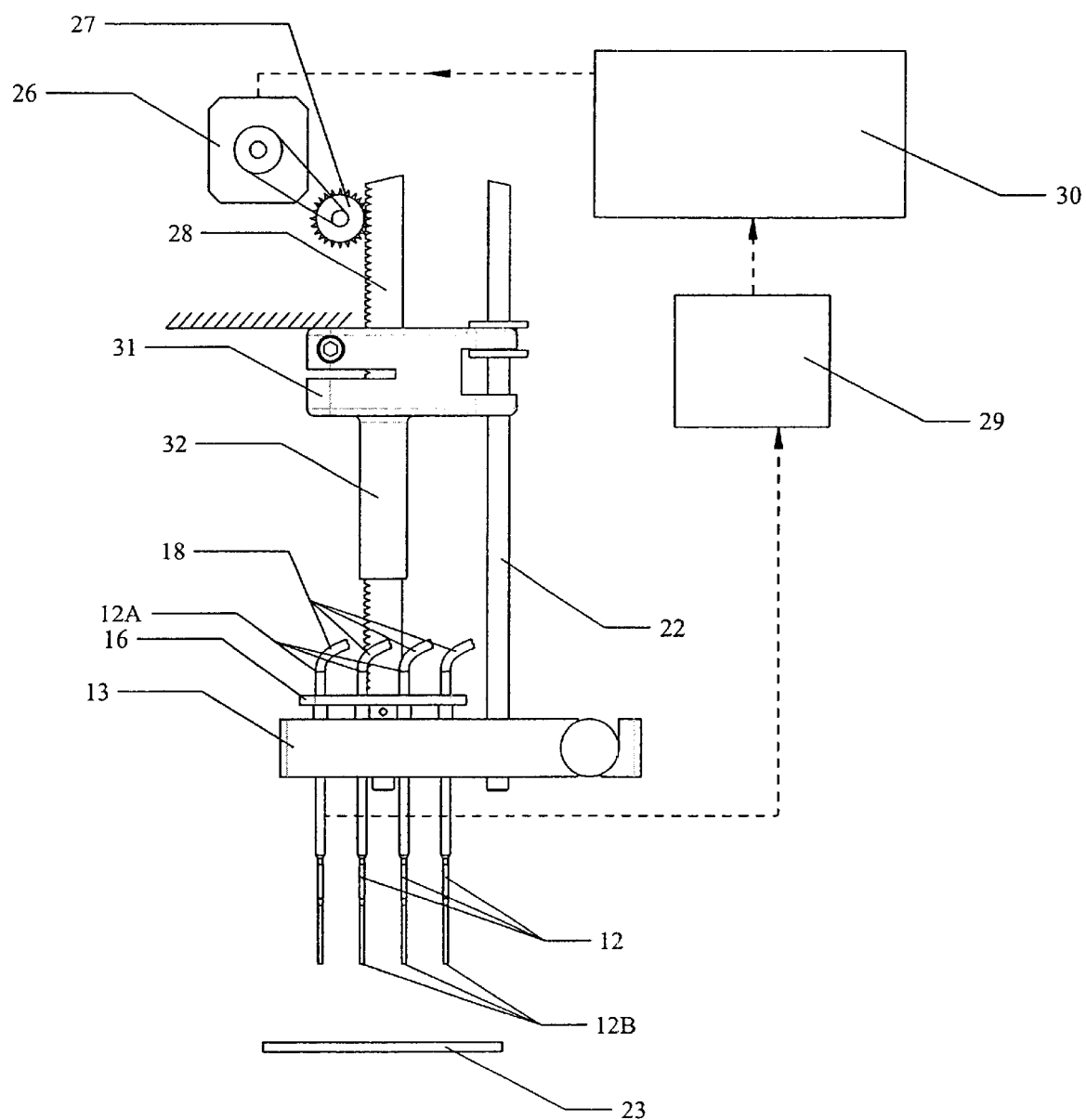
FIG. 4 is a schematic view of the system aspect of the present invention.

Referring to FIGS. 1, 2 and 4, an array of probes is shown positioned within a movable probe housing, the movement of which causes the probes to move up or down in the Z direction. While robotic systems that include such probes are used in a wide variety of applications, one particularly preferred embodiment is a computer controlled, mass spectrometry robotic workstation. One such workstation used to automate the handling and preparation of samples for MALDI MS analysis is the Symbiot® sample workstation (Applied Biosystems, Foster City, Calif.). This workstation has enjoyed commercial success by exhibiting an ability to rapidly and reliably handle and dispense small volumes of liquid samples, despite employing only a single probe.

The probe apparatus 10 includes a plurality of probes 12 formed as hollow tubes, such as the 4×4 array shown, contained within a probe housing 13. The probes 12 are each positioned within a slip fit bore 14 that extends through the cross-section of the housing in a manner which permits each of the probes 12 to move in a Z direction within their respective slip bores 14. The probe housing 13 is attached to reset plate 16. The inlet end 12A of the probe 12 is attached to and is in fluid communication with flexible conduits 18. The flexible conduits 18 are in fluid communication with a source of fluid pressure such as a syringe pump (not shown) which activates the flow of a fluid such as wash water within the flexible conduits 18. Each probe 12 is retained in place within its respective bore 14 by spring 19 which applies a frictional force to the walls of each probe 12.

The probe housing 13 is attached to a motor driven rack 28 and to a guide post 22. The motor driven rack 28 is activated by motor 26 which, in turn, is activated and controlled by a conventional computer or minisample processor 30 of the robotic system. The control of the movement of robotic components such as probe housing 13 is well known in the art as many robot systems are commercially available. One such system that has been found to work well with the present invention is the MSP 9500 mini sample processor available from Cavro Scientific Instruments, Inc., Sunnyvale, California. The computer 30 also controls pressure within the probes 12 so that fluid can be either aspirated into or expelled therefrom in a manner more fully described below.

The rack 28 extends through support element 31 that includes fixed sleeve 32 extending downwardly from support element 31. The sleeve 32 functions to contact reset plate 16 to reset the position of the probes to an initial position as described below.

Figure 3:
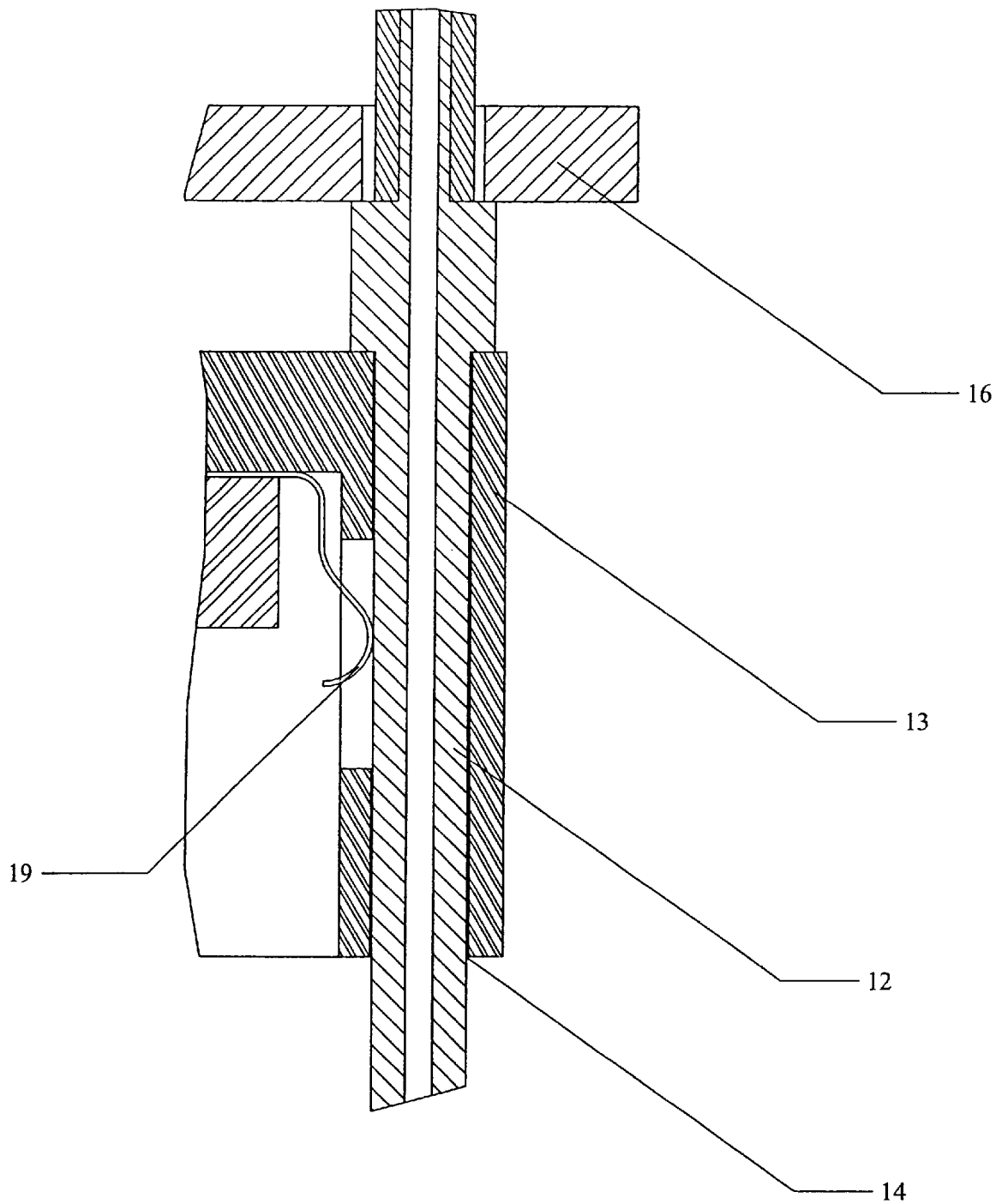
FIG. 3 is a cross-sectional side view of a probe and probe housing of a preferred embodiment of the present invention.

Referring also to FIG. 3, an individual probe 12 is shown extending through one bore 14 of probe housing 13. The inlet end 12A of probe 12 is attached to a flexible conduit 18 and the probe also includes an outlet end 12B. The probe 12 is retained within bore 14 by spring 19 that applies a frictional force to the outside wall of probe 12. As previously explained, the magnitude of the frictional force is sufficient to retain the probe 12 in a set position while at rest within bore 14, yet of sufficiently low magnitude as to be overcome by an axial force applied to the probe either when it comes in contact with MALDI sample plate 23 (see also FIG. 4) or reset plate 16 when the reset plate 16 is contacted with fixed sleeve 32 as described below.

In use, the system of the present invention is controlled by computer 30 that controls both the X-Y (i.e. in a plane parallel to the robot deck) and Z direction motion of the probe housing 13. Inputs, including the X-Y location of various components on the robot deck (MALDI sample plate, MTP, wash/waste station), the height of the probe housing above the deck for travel between components and between locations within such components ("Z-Start"), and the height of the probe housing corresponding to the lowest position in an MTP reservoir ("Z-Max")from which to aspirate, are stored in computer 30. Computer 30 also receives an input from sensor 29 such as a capacitance sensor which measures the height of the probes 12 above the sample plate 23. To this effect all of the probes are electrically wired together and connected to sensor 29. The output of computer 30 activates motor 26 such as a stepper motor that through pinion gear 27 drives rack 28 to produce Z movement of the probe housing 13.

For MALDI MS spotting applications, a complete cycle of the robotic system includes three primary operations, namely aspiration of the sample into the probe, spotting the MALDI sample plate with sample and washing the probes for reuse. At the beginning of a cycle with probes at the Z-Start position, the pump is activated to pull air into the probes. The probe housing is then moved over the MTP and the probes are lowered to the Z-Max position of the MTP to allow aspiration of sample. The pump is re-activated and liquid sample enters the probe. The probes are retracted to the Z-Start position and another (trailing) air gap is aspirated to prevent sample from spilling out of the probe.

In the next operation the probe housing 13 is moved over the sample plate 23 to initiate sample spotting. The sensor 29 senses when the probes contact the sample plate. To avoid disrupting any materials already placed on the sample spotting position, the probes contact the plate adjacent to the actual spotting region. After contact, computer 30 activates motor 26 and causes the motor to step a predetermined number of additional steps to overdrive the probes into the plate as previously discussed. The Z value of this plate contact position is stored in computer 30. The probes are then moved to the Z-Start position above the sample plate. The trailing air gap is dispensed prior to lowering the probes to the spotting dispense height, which is determined by subtracting a small distance (e.g., 0.01 inch) from the previously stored plate contact value. The pump is activated to dispense sample at the desired location on the sample plate. Depending on the volume of sample to be dispensed, computer 30 may cause the probes to retract at the same time dispensing occurs to prevent the sample to be spotted from bulging or moving to the side of the probe.

After dispensing of the sample is completed, the probe housing 13 is raised to contact the sleeve 32 to reset the probes to their initial position. The probe housing is then moved to a waste station (not shown) where any remaining sample is dispensed. The probes 12 then are immersed in a wash station while the pressure within the conduits 18 is increased in order to dispense wash liquid into probes 12 to clean the probes 12. The substrate surface 23 then is replaced with a new substrate surface and the cycle is repeated.

It is to be understood that means other than a spring 19 can be utilized to apply the frictional force to the probes 12, such as on O-ring, a flexible conduit or the like. It is also possible to apply gravity forces against the probe by adapting the probe housing 13 in the vicinity of the probe to permit an additional element, such as a wedge, ball or any other appropriate shape, to be inserted to produce a frictional force against the walls of the probe 12.

What is claimed is:

1. Apparatus for delivering fluid samples to a substrate surface comprising:
    a probe housing;
    a plurality of probes having an internal conduit adapted to be connected to a sample source for receiving and passing a fluid sample therethrough, each probe positioned within a bore in the probe housing;
    a friction element adapted to apply a frictional force to each of the probes of sufficient magnitude to retain the probes within the probe housing;
    a probe driver adapted to move the probe housing toward or away from the substrate surface;
    wherein in response to the probes contacting the substrate surface an axial force in excess of the frictional force is applied to the probes to move at least some of the probes from their initial position to a new position, and wherein in the absence of the application of the axial force the probes are retained at the new position.

2. The apparatus of claim 1 wherein the friction element is a spring.

3. The apparatus of claim 1 wherein the friction element is an O-ring.

4. The apparatus of claim 1 further comprising a controller operatively coupled to the probe driver and adapted to over drive the probe housing after initial contact with the substrate surface.

5. A system for dispensing a plurality of liquid samples from a desired height comprising:
    a substrate with a surface for receiving the liquid sample;
    a probe housing having a plurality of bores extending therethrough;
    a plurality of probes each positioned within a respective bore and each having an internal conduit adapted to be connected to a sample source for receiving and passing a liquid sample therethrough;
    a friction element adapted to apply a frictional force to each of the probes of sufficient magnitude to retain the probes within the probe housing;
    a probe driver adapted to move the probe housing with respect to the substrate surface;
    a controller operatively coupled to the probe driver for controlling the movement of the probe housing and the intake and expulsion of the liquid sample within the internal conduit of the probe;
    wherein in response to the probes contacting the substrate surface an axial force in excess of the frictional force is applied to the probes to move at least some of the probes from their initial position to a new position; and
    wherein in response to the controller the probe housing is caused to move a predetermined distance above the surface of the substrate after contact therewith such that the axial force is no longer applied and the frictional force retains the probes in the new position to effect accurate dispensing of liquid sample on the surface of the substrate.

6. The system of claim 5 wherein the friction element is a spring.

7. The system of claim 5 wherein the friction element is an O-ring.

8. The system of claim 5 wherein the controller is adapted to over drive the probe housing after initial contact with the substrate surface.

9. The system of claim 5 wherein the substrate is a MALDI sample plate.

10. A process for delivering a plurality of fluid samples to a substrate surface comprising the steps of:

provosting a plurality of probes each positioned within a respective bore of a probe housing and each having an internal conduit adapted to be connected to a sample source for receiving and passing a liquid sample therethrough;

applying a frictional force to each of the probes of sufficient magnitude to retain the probes within the probe housing;

contacting the probes with the substrate surface to apply a second force to the probes sufficient to overcome the frictional force to move at least some of the probes from an initial position to a new position.

11. The process of claim 10 further comprising the steps of:

aspirating a volume of air into the internal conduit of the probes;

aspirating a liquid sample into the internal conduit of the probes;

moving the probe housing to a desired height above the substrate surface; and depositing the liquid samples from the probes onto the substrate surface.

12. The process of claim 11 further comprising the steps of:

washing the internal conduit of the probes; and applying a third force to move the probes back to their initial position.

13. The process of claim 12 wherein the third force is applied to a plate in contact with all of the probes.

14. Apparatus for delivering a plurality of samples to a substrate surface comprising:

a probe housing;

a plurality of probes positioned within a bore in the probe housing;

a friction element adapted to apply a frictional force to each of the probes of sufficient magnitude to retain the probes within the probe housing;

a driver adapted to move the probe housing toward or away from the substrate surface;

wherein in response to the probes contacting the substrate surface a second force in excess of the frictional force is applied to the probes to move at least,some of the probes from their initial position to a new position, and wherein in the absence of the application of the axial force the probes are retained at the new position.

15. The apparatus of claim 14 wherein in the absence of the application of the second force the probes are retained at the new position.

16. Apparatus for delivering fluid samples to a substrate surface which comprises:

a plurality of probes having an internal conduit for passing a fluid therethrough, each of the probes positioned within a bore in a probe housing;

a friction element adapted to apply a frictional force to the probes to retain the probes within the housing;

means for applying a second force to the probes in excess of the frictional force to contact an outlet end of the probes with the substrate surface whereby the probes are moved from an initial position;

means for aspirating a fluid sample into the internal conduit of the probes; and means for expelling the fluid samples from the conduits onto a solid substrate surface.

17. The apparatus of claim 16 further comprising means for applying a third force to the probes which is in excess of the frictional force to return the probes to the initial position.

18. The apparatus of claim 16 wherein the friction element comprises a spring.

19. The apparatus of claim 16 wherein the friction element is an O-ring.

20. The apparatus of claim 16 wherein the substrate is a MALDI sample plate.

\* \* \* \* \*